US00PP22054P2

(12) United States Plant Patent

Klemm et al.

(10) Patent No.: US PP22,054 P2

(45) Date of Patent: Aug. 2, 2011

(54) *OSTEOSPERMUM* PLANT NAMED 'KLEOE09175'

(50) Latin Name: *Osteospermum ecklonis* Norl.
Varietal Denomination: KLEOE09175

(75) Inventors: Nils Klemm, Stuttgart (DE); Andrea Dohm, Pforzheim (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 12/798,190

(22) Filed: Mar. 31, 2010

(51) Int. Cl.
*A01H 5/00* (2006.01)

(52) U.S. Cl. ..... Plt./360

(58) Field of Classification Search ..... Plt./360
See application file for complete search history.

*Primary Examiner* — Susan McCormick Ewoldt

(74) *Attorney, Agent, or Firm* — Jondle & Associates, P.C.

(57) ABSTRACT

An *Osteospermum* variety named 'KLEOE09175' particularly distinguished by bicolor amethyst copper flowers, round petals, very tolerant to various weather conditions, a very early flowering time, and a semi-upright growth habit, is disclosed.

1 Drawing Sheet

Genus and species: *Osteospermum ecklonis* Norl.
Variety denomination: 'KLEOE09175'.

BACKGROUND OF THE NEW PLANT

The present invention comprises a new and distinct variety of *Osteospermum*, botanically known as *Osteospermum ecklonis* Norl., and hereinafter referred to by the variety name 'KLEOE09175'. The new variety was discovered as a seedling resulting from a cross conducted in August 2006 in Stuttgart, Germany. The female parent was the *Osteospermum* plant named 'Astra Pink Yellow' (unpatented), and the male parent was a proprietary *Osteospermum* plant named 'C101' (unpatented). A single plant selection was subsequently chosen for further evaluation and for asexual propagation.

The new variety was first propagated via vegetative cuttings in May 2007 in Stuttgart, Germany and has been asexually reproduced repeatedly by vegetative cuttings in Stuttgart, Germany for approximately 10 generations. The present invention has been found to retain its distinctive characteristics through successive asexual propagations via vegetative cuttings.

Plant Breeder's Rights for this variety have not been applied for. 'KLEOE09175' has not been made publicly available or sold more than one year prior to the filing date of this application.

SUMMARY OF THE INVENTION

The following are the most outstanding and distinguishing characteristics of the new variety when grown under normal horticultural practices in Stuttgart, Germany.

1. Bicolor amethyst copper flowers;
2. Round petals;
3. Very tolerant to various weather conditions;
4. A very early flowering time; and
5. A semi-upright growth habit.

DESCRIPTION OF THE PHOTOGRAPH

This new *Osteospermum* plant is illustrated by the accompanying photograph which shows a close-up of the flower of the plant. The colors shown are as true as can be reasonably obtained by conventional photographic procedures. The photograph was taken in Summer 2009 of a 7-month-old plant in the field in Stuttgart, Germany, under conditions which approximate those generally used in commercial practice.

DESCRIPTION OF THE NEW VARIETY

The following detailed descriptions set forth the distinctive characteristics of 'KLEOE09175'. The data which define these characteristics were collected from asexual reproductions carried out in Stuttgart, Germany. The plant history was taken in Summer 2009 on 7-month-old plants which were potted at 4 weeks in 12 centimeter containers and then planted in the ground in calendar week 20. The plants were pinched once at 6 weeks. Color readings were taken under natural light. Color references are primarily to The R.H.S. Colour Chart of The Royal Horticultural Society of London (R.H.S.), Fifth Edition (2007).

DETAILED BOTANICAL DESCRIPTION OF THE NEW PLANT

Classification:
- *Family.*—Asteraceae.
- *Botanical name.*—*Osteospermum ecklonis* Norl.
- *Common name.*—African daisy.

Parentage:
- *Female parent.*—The *Osteospermum* plant named 'Astra Pink Yellow' (unpatented).
- *Male parent.*—A proprietary *Osteospermum* plant named 'C101' (unpatented).

Plant:
- *Form and habit.*—Semi-upright (V-shape).
- *Growth habit.*—Compact.
- *Branching habit.*—Excellent branching.
- *Height (from top of soil, including inflorescence).*—37.0 cm to 40.0 cm.
- *Width (including inflorescences).*—40.0 cm to 45.0 cm.
- *Propagation.*—Vegetative cuttings.

*Time to produce a finished flowering plant.*—15 weeks from sticking.
*Time to initiate and develop roots.*—3 weeks.
*Root description.*—Freely rooting.

Leaves:
*Arrangement.*—Alternate.
*Shape.*—Obovate.
*Apex.*—Acute.
*Base.*—Acute.
*Margin.*—Serrate.
*Color.*—Immature leaf (both surfaces): RHS 146B. Mature leaf: Upper surface: RHS 146B. Lower surface: RHS 146C.
*Length.*—5.0 cm to 6.0 cm.
*Width.*—2.1 cm to 2.4 cm.
*Texture.*—Glabrous on the upper surface.
*Appearance.*—Leathery on the upper surface.
*Petioles.*—Absent.
*Venation pattern.*—No venation.

Stems:
*Total number of branches per plant* (*calculated at the base of the plant*).—Approximately 10.
*Length.*—35.0 cm to 40.0 cm.
*Diameter.*—0.2 cm to 0.9 cm.
*Internode length.*—0.3 cm to 0.7 cm.
*Color.*—RHS 144B.
*Texture.*—Rough.
*Appearance.*—Rough.
*Anthocyanin.*—Absent.

Inflorescence buds:
*Shape.*—Obovate.
*Length.*—1.5 cm.
*Diameter.*—0.8 cm.
*Color* (*at tight bud just before the ray florets unfold*).—RHS 143B.

Inflorescence:
*Type.*—Composite, single.
*Blooming habit.*—Plants flower continuously from early Spring to Fall.
*Quantity of inflorescences per plant.*—Approximately 200.
*Lastingness of the inflorescences on the plant.*—10 days.
*Fragrance.*—Absent.
*Inflorescence diameter.*—5.0 cm to 7.0 cm.
*Inflorescence depth.*—Approximately 1.5 cm.
*Disc diameter.*—1.0 cm.

Disc floret:
*Quantity per inflorescence.*—Approximately 50.
*Shape.*—Tubular, radially symmetrical.
*Tube color.*—Closed: RHS 148C. Mature: RHS 2D.
*Length.*—Approximately 0.5 cm.
*Diameter* (*at apex*).—0.2 cm to 0.3 cm.
*Apex.*—Acuminate.
*Apex color.*—RHS 2D.
*Base.*—Obtuse.
*Base color.*—RHS 2D.
*Margin.*—Entire.

Ray floret:
*Quantity per inflorescence.*—Approximately 18.
*Shape.*—Obovate.
*Color.*—Upper surface: RHS 77A on the top, RHS 63A in the middle, and RHS 164C at the bottom. Lower surface: RHS 11B to RHS 4D, and RHS N79D.
*Length.*—2.5 cm to 3.5 cm.
*Width.*—0.8 cm.
*Apex.*—Obtuse.
*Base.*—Acute.
*Margin.*—Entire.
*Texture.*—Smooth.
*Peduncle.*—Length: 10.0 cm to 15.0 cm. Diameter: 0.2 cm. Texture: Rough. Color: RHS 141C.

Phyllaries:
*Arrangement.*—Single.
*Observed quantity per plant.*—Approximately 18.
*Shape.*—Lanceolate.
*Color.*—Upper surface: RHS 146B. Lower surface: RHS 139C.
*Length.*—0.9 cm to 1.2 cm.
*Width.*—0.2 cm.
*Apex.*—Acute.
*Base.*—Obtuse.
*Margin.*—Entire.
*Texture.*—Rough.

Reproductive organs:
*Androecium.*—Location: On the disc floret. Stamens: Quantity: Numerous. Shape: Tubular. Filament length: 0.5 cm to 0.9 cm. Filament diameter: 0.1 cm to 0.2 cm. Anther: Shape: Longitudinal. Color: RHS 155C. Length: 0.2 cm. Diameter: 0.02 cm. Pollen: Color: RHS 125A. Amount: Moderate.
*Gynoecium.*—Location: On the base of the petals (ray floret). Pistils: Number: 17. Length: 0.3 cm. Diameter: 0.05 cm. Stigma: Color: RHS 7A. Shape: Ovate. Length: 0.05 cm. Diameter: 0.02 cm. Style: Color: RHS 7A. Length: 0.25 cm. Diameter: 0.05 cm.

Fruit and seed set: Dark brown, torpedo-shaped seeds; moderate seed set observed.

Disease and insect resistance: No particular disease or insect resistance observed.

COMPARISON WITH PARENTAL AND COMMERCIAL VARIETIES

'KLEOE09175' differs from the female parent, the *Osteospermum* plant named 'Astra Pink Yellow' (unpatented) in that 'KLEOE09175' has a semi-upright, medium vigorous growth habit, whereas 'Astra Pink Yellow' has a very compact growth habit. In addition, 'KLEOE09175' has bicolor amethyst copper flowers that are very tolerant to various weather conditions, whereas 'Astra Pink Yellow' has bicolor yellow violet flowers with soft petals that are not very tolerant to various weather conditions.

'KLEOE09175' differs from the male parent, the proprietary *Osteospermum* plant named 'C101' (unpatented) in that 'KLEOE09175' has bicolor amethyst copper flowers, and 'C101' has light copper flowers. In addition, 'KLEOE09175' flowers earlier than 'C101'.

'KLEOE09175' differs from the commercial variety 'Siena' (unpatented) in that 'KLEOE09175' has bicolor amethyst copper flowers with round petals, whereas 'Siena' has flowers that are more of a red color, with narrower petals. In addition, 'KLEOE09175' flowers earlier than 'Siena'.

We claim:

1. A new and distinct variety of *Osteospermum* plant named 'KLEOE09175' as shown and described herein.

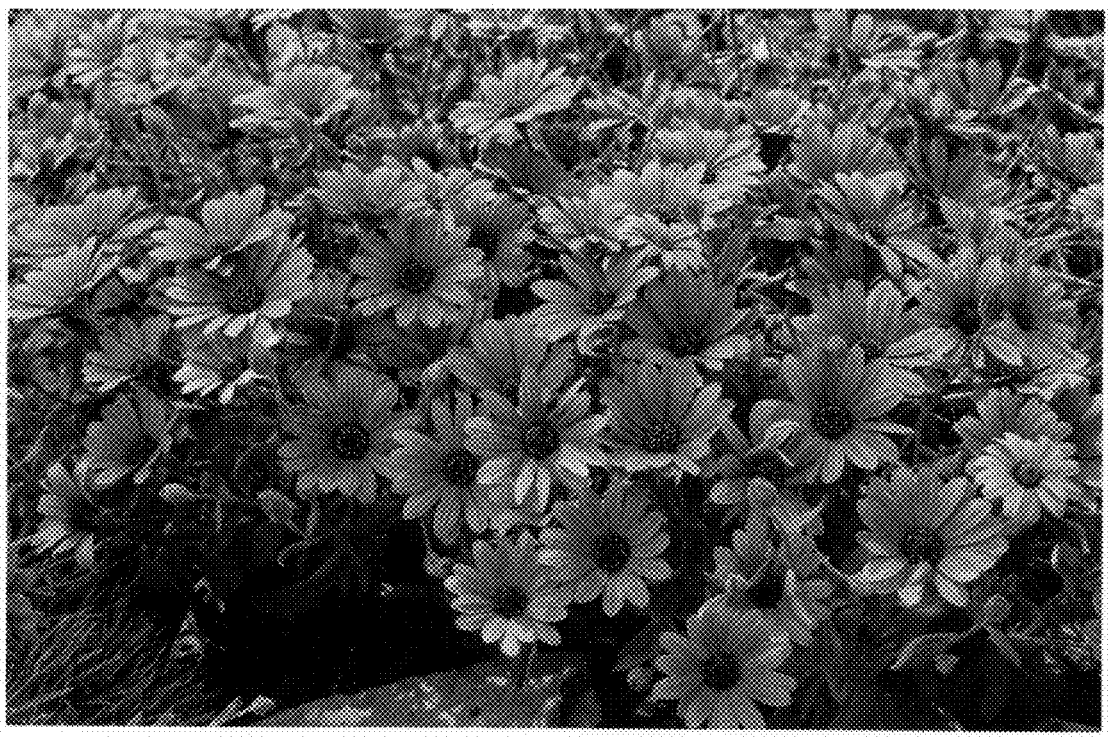

* * * * *